United States Patent [19]

Buck et al.

[11] Patent Number: 4,895,584
[45] Date of Patent: Jan. 23, 1990

[54] PROCESS FOR $C_2$ RECOVERY

[75] Inventors: Loren L. Buck, Tulsa; Ronald D. Key, Broken Arrow, both of Okla.

[73] Assignee: Pro-Quip Corporation, Ponca City, Okla.

[21] Appl. No.: 296,432

[22] Filed: Jan. 12, 1989

[51] Int. Cl.⁴ .................................................. F25J 3/02
[52] U.S. Cl. .......................................... 62/29; 62/24; 62/31
[58] Field of Search .................. 62/23, 24, 27, 28, 29, 62/31

[56] References Cited

U.S. PATENT DOCUMENTS

| | | | |
|---|---|---|---|
| 3,702,541 | 11/1972 | Randall et al. | 62/24 |
| 4,171,964 | 10/1979 | Campbell et al. | 62/24 |
| 4,272,270 | 6/1981 | Higgins | 62/24 |
| 4,617,039 | 10/1986 | Buck | 62/31 |
| 4,711,651 | 12/1987 | Sharma et al. | 62/24 |
| 4,758,258 | 7/1988 | Mitchell et al. | 62/29 |

*Primary Examiner*—Ronald C. Capossela
*Attorney, Agent, or Firm*—Head & Johnson

[57] ABSTRACT

An improved process for separating a hydrocarbon bearing feed gas containing methane and lighter, $C_2$ (ethylene and ethane) and heavier components into a fraction containing predominantly methane and lighter components and a fraction containing predominantly $C_2$ and heavier hydrocarbon components including the steps of cooling and partially condensing and delivering the feed stream to a separator to provide a first residue vapor and a $C_2$ containing liquid, directing a portion of the $C_2$ containing liquid into a heavy ends fractionation column wherein the liquid is separated into a second hydrocarbon bearing vapor residue and a $C_2$ containing product, conducting a portion of the first residue vapors with at least part of the partially condensed second residue into a light ends fractionating column to thereby obtain third residue vapors and liquids, supplying the liquids recovered from the light ends fractionating column to the heavy ends fractionation column as the liquid feed thereto and directing part of the $C_2$ containing liquid from the first step into intimate contact with the second residue, which liquid provides additional liquefied methane which acts with the partially condensed second residue as a direct contact refrigerant to thereby condense $C_2$ and heavier components while the methane itself is evaporated in the light ends fractionation column.

16 Claims, 4 Drawing Sheets

PROCESS FOR C₂ RECOVERY

SUMMARY OF THE INVENTION

This invention provides an improved process for separating a hydrocarbon bearing feed gas which contains methane and lighter component, (not necessarily all hydrocarbon components), $C_2$ (ethylene and ethane) and heavier hydrocarbon components into two fractions. The first fraction contains predominantly methane and lighter components and the second fraction contains the recovered desirable $C_2$ and heavier components.

Hydrocarbon bearing gas contains lighter components (e.g. hydrogen, nitrogen, etc.) methane, ethane and a substantial quantity of hydrocarbons of higher molecular weight, for example, propane, butane, pentane and often their unsaturated analogs. Recent changes in ethylene demand have created increased markets for ethylene and have created a need for more efficient processes which yield higher recovery levels of this product. In more recent times the use of cryogenic processes utilizing the principle of gas expansion through a mechanical device to produce power while simultaneously extracting heat from the system have been employed. The use of such equipment depending upon the pressure of the gas source, the composition of the gas and the desired end results. In the typical cryogenic expansion-type recovery processes used in the prior art, a gas stream under pressure is cooled by heat exchange with other streams of the process and/or external sources of cooling are employed such as refrigeration systems. As the gas is cooled, liquids are condensed and are collected and separated so as to thereby obtain desired hydrocarbons. The high pressure liquid feed is typically transferred to a demethanizer column after the pressure is adjusted to the operating pressure of the demethanizer. In such fractionating column the liquid feed is fractionated to separate the residual methane and lighter components from the desired products of ethylene/ethane and heavier hydrocarbon components. In the ideal operation of such separation processes, the vapors leaving the process contain substantially all of the methane and lighter components found in the feed gas and substantially no ethylene/ethane or heavier hydrocarbon components remain. The bottom fraction leaving the demethanizer typically contains substantially all of the ethylene/ethane and heavier hydrocarbon components with very little methane or lighter components which is discharged in the fluid gas outlet from the demethanizer. The present invention provides processes for increasing the ethane and ethylene component of the liquid discharge from the process unit.

This advantage is achieved in the present invention by a process in which the feed gas is first cooled and partially condensed and delivered to a separator to provide a first residue vapor and a $C_2$ containing liquid which liquid also contains lighter hydrocarbons. Part of the $C_2$ containing liquid from the separator may be directed into a heavy ends fractionation column, wherein the liquid is separated into a second residue containing lighter hydrocarbons and $C_2$ containing products. A part of the first residue vapors with at least part of the partially condensed second residue are counter currently contacted and co-mingled in a light ends fractionating column to thereby provide third residue vapors and liquids which are separately discharged. The liquids recovered from the light ends fractionating column are then fed to the heavy ends fractionation column as a liquid feed. A portion of the $C_2$ containing liquids from the separator is fed into intimate contact with the second residue prior to discharging the co-mingled liquids and gases into the light ends fractionating column to thereby achieve mass and heat transfer and to thereby liquefy a higher percent of the $C_2$ and heavier hydrocarbon components while the methane is vaporized.

In this manner a higher proportion of the $C_2$ and heavier hydrocarbon components are recovered.

Other prior issued U.S. patents which relate to processes for recovering lighter hydrocarbons from a gas stream include the following U.S. Pat. Nos.: 4,272,270; 4,356,014; 4,486,209; 4,582,517; 4,592,766; 4,596,588; 4,597,788; 4,600,421 and 4,707,171. Others have provided methods for $C_3$ (propylene/propane) methods exemplified by U.S. Pat. No. 4,617,039 assigned to The Pro-Quip Corporation. U.S. Pat. No. 4,707,171, appears to be a logical extension of U.S. Pat. No. 4,617,039 applied to $C_2$ recovery.

A better understanding of the invention will be had with reference to the following description and claims, taken in conjunction with the attached drawings.

DESCRIPTION OF THE PREFERRED EMBODIMENTS

The improved processes of the present disclosure include the steps of cooling a gaseous hydrocarbon-containing feed stream to form a vapor stream and a liquid stream. The liquid stream may be partially transferred to a heavy ends fractionation column while the vapor stream is expanded and transferred to the bottom of a light ends fractionation column. The heavy ends fractionation column overhead, which consists mainly of methane and ethane, is cooled and fed to the upper portion of the light ends fractionation column. The liquid flows downwardly within the light ends fractionation column and contacts gaseous ethylene and heavier hydrocarbons that flow upwardly. The methane portion of the liquid stream is vaporized by absorbing heat from the gaseous ethylene and heavier hydrocarbons which causes the ethylene and heavier hydrocarbons to condense and exit at the bottom of the light ends fractionation column. The gaseous methane and lighter components within the light ends fractionation column are removed from the overhead as a product of the process. The liquid at the bottom of the light ends fractionation column is removed and fed to the upper portion of the heavy ends fractionation column. The liquid at the bottom of the heavy ends fractionation column is removed as a product of the process and at least a portion of the gaseous overhead is cooled and returned to the top of the light ends fractionation column.

Figure 1:
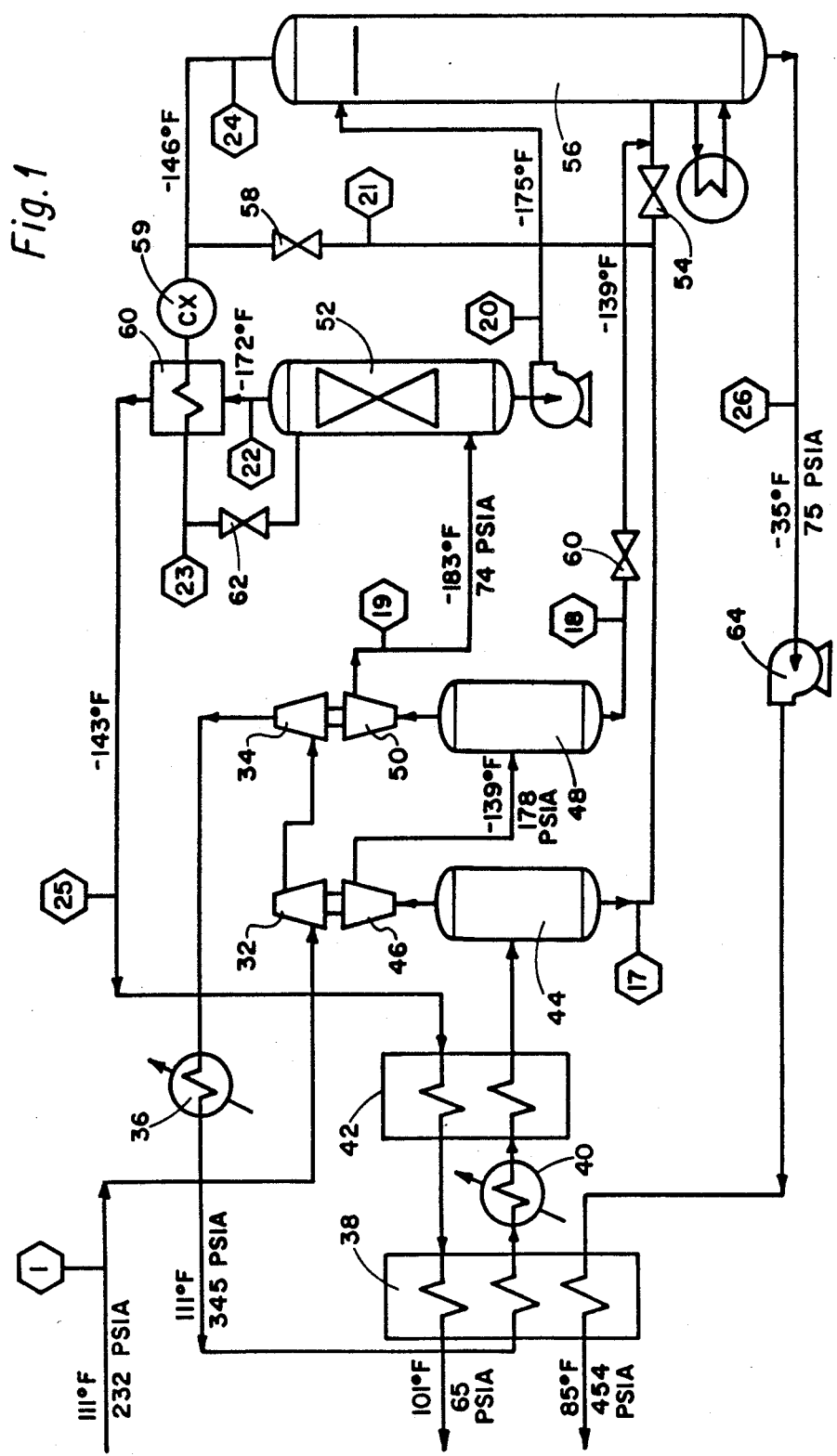
FIG. 1 is a schematic flow diagram illustrating a method of practicing a preferred embodiment of the invention.

The improved process of this invention is illustrated in a first embodiment in FIG. 1. The incoming gas stream 1 is first fed to a booster compressor 32 and from the output thereof to a second booster compressor 34.

The stream then flows through a heat exchanger 36. The gas exits from heat exchanger 36 at a temperature of 111° F., but the pressure thereof has been raised to 345 psia. The gas then passes through heat exchangers 38, 40 and 42 so that the temperature thereof is reduced to about −98° F. Pressure is dropped as the gas flows through the heat exchangers resulting in a pressure of 335 psia at −98° F., at which the raw gas is delivered into a high pressure separator 44. Within separator 44 the cooled gas stream is separated into a first residue vapor which is passed through a turbo expander 46. The shaft of turbo expander 46 is connected directly to the shaft of the first booster compressor 32. From the first turbo expander, the first residue gas having a temperature of about −139° F. at 178 psia passes through a second high pressure separator 48. The residue vapor therefrom passes through a second turbo expander 50. The gas from the second turbo expander passes by way of stream 19 at a temperature of about −183° F. and 74 psia into a light ends fractionating column 52.

From the first high pressure separator 44, by way of stream 17, the $C_2$ containing liquid is channeled in two directions. Through valve 54 the $C_2$ containing liquid is conducted into a heavy ends fractionation 56. All or a portion of the liquid from the first high pressure separator 44 may also pass by way of stream 21 and valve 58 for introduction into the light ends fractionating column 52 in a manner and for purposes to be described subsequently.

The liquid discharge from the second high pressure separator 48 is conveyed by stream 18 through valve 60 into the heavy ends fractionation column 56. Stream 18 is at a temperature of about −139° F.

The off gas from heavy ends fractionation column 56, having a temperature of about −146° F., is fed by stream 24 through heat exchangers 59 and 60 and by way of stream 23 and valve 62 into the upper end of the light ends fractionating column 52. At least a portion of the liquid residue from high pressure separator 44, is recycled by stream 21 and co-mingled with the off gas passing through stream 24 from heavy ends fractionation column 56. This co-mingled liquid and gas stream is then passed by the stream 23 back into the light ends fractionating column 52. The liquid from stream 23 passes downwardly through the light ends fractionating column 52 and encounters the rising off gas from stream 19 so that mass and latent heat transfer occur.

The light ends fractionating column 52 functions as a combination heat and mass transfer device. The column has two feed streams; that is, streams 19 and 23, and two product streams; that is, streams 20 and 22. The light ends fractionating column 52 consists of at least one, and preferably more, liquid-vapor equilibrium stages.

The methane and lighter constituents and unrecovered ethylene and ethane, exit as a dew point vapor from the top tray or separation stage of the light ends fractionating column 52. Vapors enter by way of stream 19 as a bottom feed while the top feed is by way of stream 23 which is a liquid enriched by a condensed methane.

The top feed through stream 23 into the light ends fractionating column 52, and particularly the methane content thereof serves as a reflux in the column. In flowing from stage to stage within column 52, the liquid methane is vaporized and in turn the liquid is progressively enriched in ethylene and ethane condensed from the upflowing bottom feed vapors from stream 19.

The liquid discharge from the lower end of the heavy ends fractionation column 56 is passed by way of stream 26 wherein the temperature thereof is about 31 35° F. and 75 psia through a pump 64 wherein the pressure is raised to about 454 psia. This discharge liquid stream passes through heat exchanger 38 which provides the final discharge temperature of the residue liquid from the system.

The off gas discharged from light ends fractionating column 52, after passing through heat exchanger 60 is conveyed by stream 25 wherein the temperature is about −143° F., through heat exchangers 42 and 38 for discharge from the system. At this stage the off gas has a temperature of 101° F. and a pressure of 65 psia. If it is desired to return the discharge gas to the same system from which the raw gas was taken, such as for further transportation of the gas, the pressure will need to be raised back up to that substantially equal to the incoming pressure of 232 psia in stream 1.

A simulation of the process of FIG. 1 is set forth in Table 1 wherein the moles per hour of various constituents of the streams are set forth. The process achieves a recovery of about 67 percent of the $C_2$ content of the feed gas in addition to substantially complete recovery of the $C_3$ and heavier hydrocarbon components of the feed gas stream.

TABLE 1

| INLET GAS | STREAM NUMBER MOL/HR | | | | | | | | | | | PERCENT RECOVERY |
| --- | --- | --- | --- | --- | --- | --- | --- | --- | --- | --- | --- | --- |
| | 1 | 17 | 18 | 19 | 20 | 21 | 22 | 23 | 24 | 25 | 26 | |
| Hydrogen | 2022.45 | 3.79 | 0.09 | 2018.57 | 0.65 | 3.79 | 2022.45 | 4.53 | 0.74 | 2022.45 | 0.00 | |
| Nitrogen | 31.57 | 0.25 | 0.01 | 31.32 | 0.10 | 0.25 | 31.57 | 0.36 | 0.11 | 31.57 | 0.00 | |
| Carbon Monoxide | 18.04 | 0.20 | 0.01 | 17.84 | 0.10 | 0.20 | 18.04 | 0.31 | 0.11 | 18.04 | 0.00 | |
| Cabon Dioxide | 6.20 | 1.09 | 0.09 | 5.02 | 2.18 | 1.09 | 4.00 | 1.16 | 0.07 | 4.00 | 2.20 | |
| Methane ($C_1$) | 293.47 | 14.10 | 0.76 | 278.61 | 13.11 | 14.10 | 292.62 | 27.12 | 13.02 | 292.62 | 0.85 | |
| Ethylene ($C_2$) | 66.25 | 23.78 | 2.01 | 40.47 | 42.85 | 23.78 | 21.81 | 24.19 | 0.42 | 21.81 | 44.44 | 67.08 |
| Ethane ($C_2$) | 167.46 | 87.83 | 8.03 | 71.60 | 129.65 | 87.83 | 30.31 | 88.36 | 0.53 | 30.31 | 137.15 | 81.90 |
| Propylene ($C_3$) | 23.96 | 21.25 | 1.49 | 1.23 | 22.04 | 21.25 | 0.45 | 21.26 | 0.02 | 0.45 | 23.51 | 98.12 |
| Propane ($C_3$) | 79.78 | 72.65 | 4.45 | 2.69 | 74.29 | 72.65 | 1.07 | 72.67 | 0.03 | 1.07 | 78.71 | 98.66 |
| 1-Butene ($C_4$) | 5.92 | 5.83 | 0.08 | 0.01 | 5.83 | 5.83 | 0.01 | 5.83 | 0.00 | 0.01 | 5.91 | 99.83 |
| Iso butane ($C_4$) | 54.13 | 53.03 | 1.00 | 0.09 | 53.04 | 53.03 | 0.09 | 53.03 | 0.00 | 0.09 | 54.04 | 99.83 |
| Butane ($C_4$) | 29.88 | 29.57 | 0.31 | 0.01 | 29.56 | 29.57 | 0.02 | 29.57 | 0.01 | 0.02 | 29.86 | 99.93 |
| Iso pentane ($C_5$) | 14.10 | 14.06 | 0.03 | 0.00 | 14.07 | 14.06 | 0.00 | 14.06 | 0.00 | 0.00 | 14.10 | 100.00 |
| Pentane ($C_5$) | 5.92 | 5.91 | 0.01 | 0.00 | 5.91 | 5.91 | 0.00 | 5.91 | 0.00 | 0.00 | 5.92 | 100.00 |
| TOTAL mol/hr | 2819.13 | 333.34 | 18.37 | 2467.46 | 393.38 | 333.34 | 2422.44 | 348.36 | 15.06 | 2422.44 | 396.69 | |
| Temperature °F. | 11 | −98 | −139 | −183 | −175 | −98 | −171 | −160 | −146 | −143 | −35 | |
| Pressure, psia | 232 | 335 | 178 | 74 | 75 | 335 | 74 | 75 | 75 | 74 | 75 | |

Figure 2:
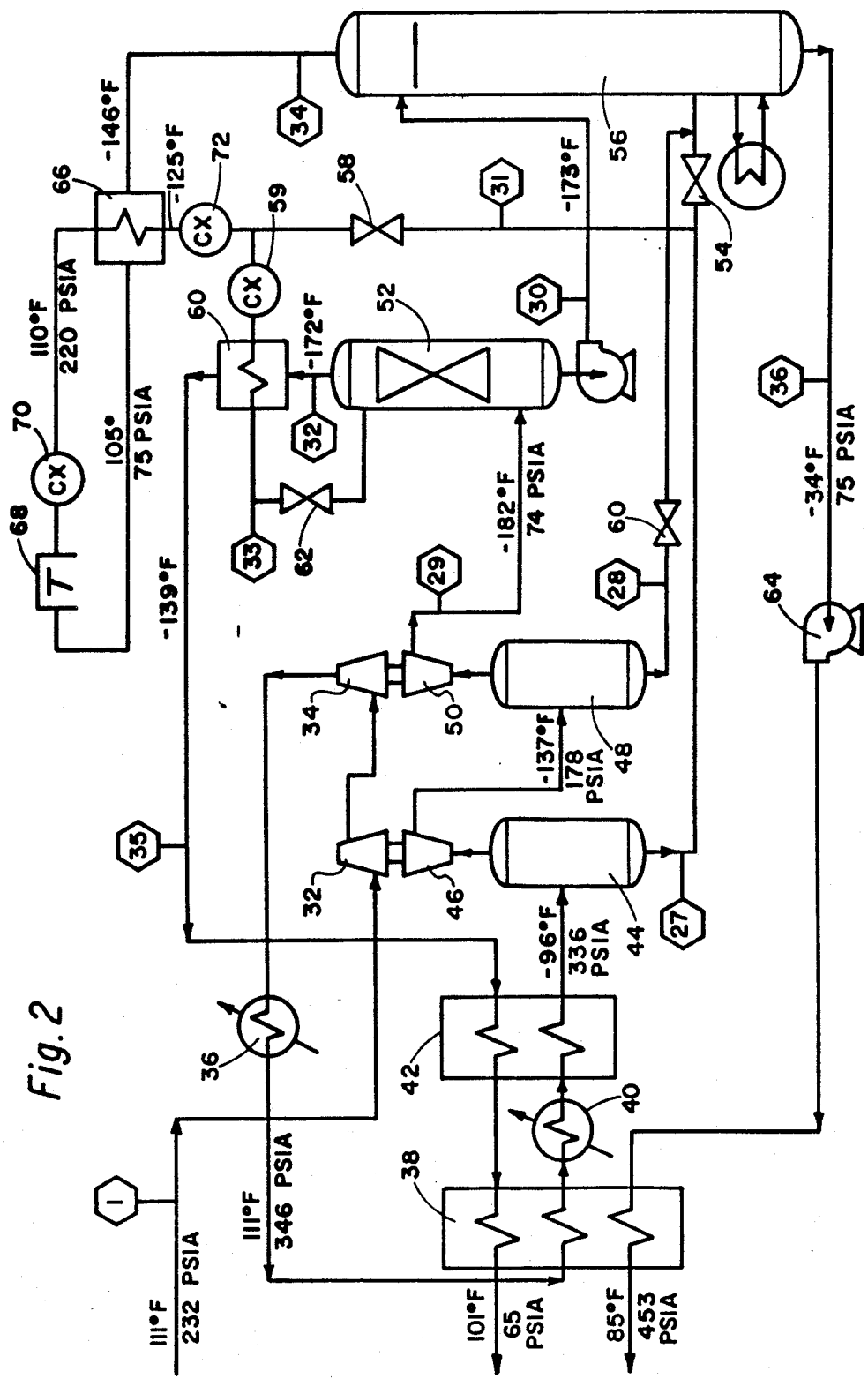
FIGS. 2 through 4 are each schematic flow diagrams illustrating variations in the preferred embodiment of the present invention.

FIG. 2 shows an alternate embodiment of the invention. The components of the process of FIG. 2 having the same basic structure and function of those of the system of FIG. 1 are given like numbers. The process is as described with reference to FIG. 1, except for the treatment of the off gas from the heavy ends fractionation column 56. In the arrangement of FIG. 2, the off embodiment of the process compared to that of the process of FIG. 1 and shows the fact that the slightly improved C₂ and heavier component recoveries are obtained by the FIG. 2 embodiment.

TABLE 2

| INLET GAS | 1 | 27 | 28 | 29 | 30 | STREAM NUMBER 31 MOL/HR | 32 | 33 | 34 | 35 | 36 | PERCENT RECOVERY |
|---|---|---|---|---|---|---|---|---|---|---|---|---|
| Hydrogen | 2022.45 | 3.78 | 0.10 | 2018.58 | 0.66 | 3.78 | 2022.45 | 4.54 | 0.76 | 2022.45 | 0.00 | |
| Nitrogen | 31.57 | 0.24 | 0.01 | 31.32 | 0.10 | 0.24 | 31.57 | 0.35 | 0.11 | 31.57 | 0.00 | |
| Carbon Monoxide | 18.04 | 0.20 | 0.01 | 17.84 | 0.10 | 0.20 | 18.04 | 0.30 | 0.10 | 18.04 | 0.00 | |
| Carbon Dioxide | 6.20 | 1.05 | 0.09 | 5.07 | 2.12 | 1.05 | 4.07 | 1.12 | 0.07 | 4.07 | 2.13 | |
| Methane | 293.47 | 13.67 | 0.76 | 279.05 | 12.79 | 13.67 | 293.02 | 26.77 | 13.10 | 293.02 | 0.45 | |
| Ethylene | 66.25 | 22.97 | 2.00 | 41.28 | 42.92 | 22.97 | 21.76 | 23.40 | 0.43 | 21.76 | 44.49 | 67.15 |
| Ethane | 167.46 | 85.37 | 8.06 | 74.03 | 130.96 | 85.37 | 29.00 | 85.93 | 0.56 | 29.00 | 138.46 | 82.68 |
| Propylene | 23.96 | 21.07 | 1.55 | 1.34 | 22.00 | 21.07 | 0.41 | 21.07 | 0.00 | 0.41 | 23.55 | 98.29 |
| Propane | 79.78 | 72.13 | 4.68 | 2.97 | 74.12 | 72.13 | 0.98 | 72.15 | 0.02 | 0.98 | 78.80 | 98.77 |
| 1-Butene | 5.92 | 5.82 | 0.09 | 0.01 | 5.82 | 5.82 | 0.01 | 5.82 | 0.00 | 0.01 | 5.91 | 99.83 |
| Iso butane | 54.13 | 52.93 | 1.09 | 0.11 | 52.96 | 52.93 | 0.08 | 52.93 | 0.00 | 0.08 | 54.05 | 99.85 |
| Butane | 29.88 | 29.53 | 0.33 | 0.02 | 29.53 | 29.53 | 0.02 | 29.53 | 0.00 | 0.02 | 29.86 | 99.93 |
| Iso pentane | 14.10 | 14.06 | 0.04 | 0.00 | 14.06 | 14.06 | 0.00 | 14.06 | 0.00 | 0.00 | 14.10 | 100.00 |
| Pentane | 5.92 | 5.91 | 0.01 | 0.00 | 5.91 | 5.91 | 0.00 | 5.91 | 0.00 | 0.00 | 5.92 | 100.00 |
| TOTAL mol/hr | 2819.13 | 328.73 | 18.82 | 2471.62 | 394.05 | 328.73 | 2421.41 | 343.88 | 15.15 | 2421.41 | 397.72 | |
| Temperature °F. | 11 | −96 | −137 | −182 | −173 | −96 | −172 | −169 | −146 | −139 | −34 | |
| Pressure, psia | 232 | 336 | 178 | 74 | 75 | 336 | 74 | 74 | 75 | 74 | 75 | | gas, flowing through stream 34, is passed first through a heat exchanger 66 and through a compressor 68 wherein the pressure is raised to about 220 psia. From the compressor the gas is passed through a stream cooler 70 wherein the temperature of the compressed gas is reduced to 110° F. The gas passes back through heat exchanger 66 and through a stream cooler 72 before the off gas is co-mingled with a portion of the effluent discharge from the high pressure separator 44. The co-mingled gas and effluent then passes through stream cooler 59, heat exchanger 60 and valve 62 before discharge into the upper portion of light ends fractionating column 52. Within such column the recycled liquid portion of the effluent functions in heat-exchange action with the hydrocarbon containing components of the gas passing upwardly in the fractionating column to condense and absorb at least a substantial portion of the C₂ and heavier hydrocarbon components. The arrangement of the FIG. 2 embodiment of the system compared to that of FIG. 1 provides for greater methane condensation in the combined gas and effluent inserted into the upper end of the light ends fractionating column.

Figure 3:
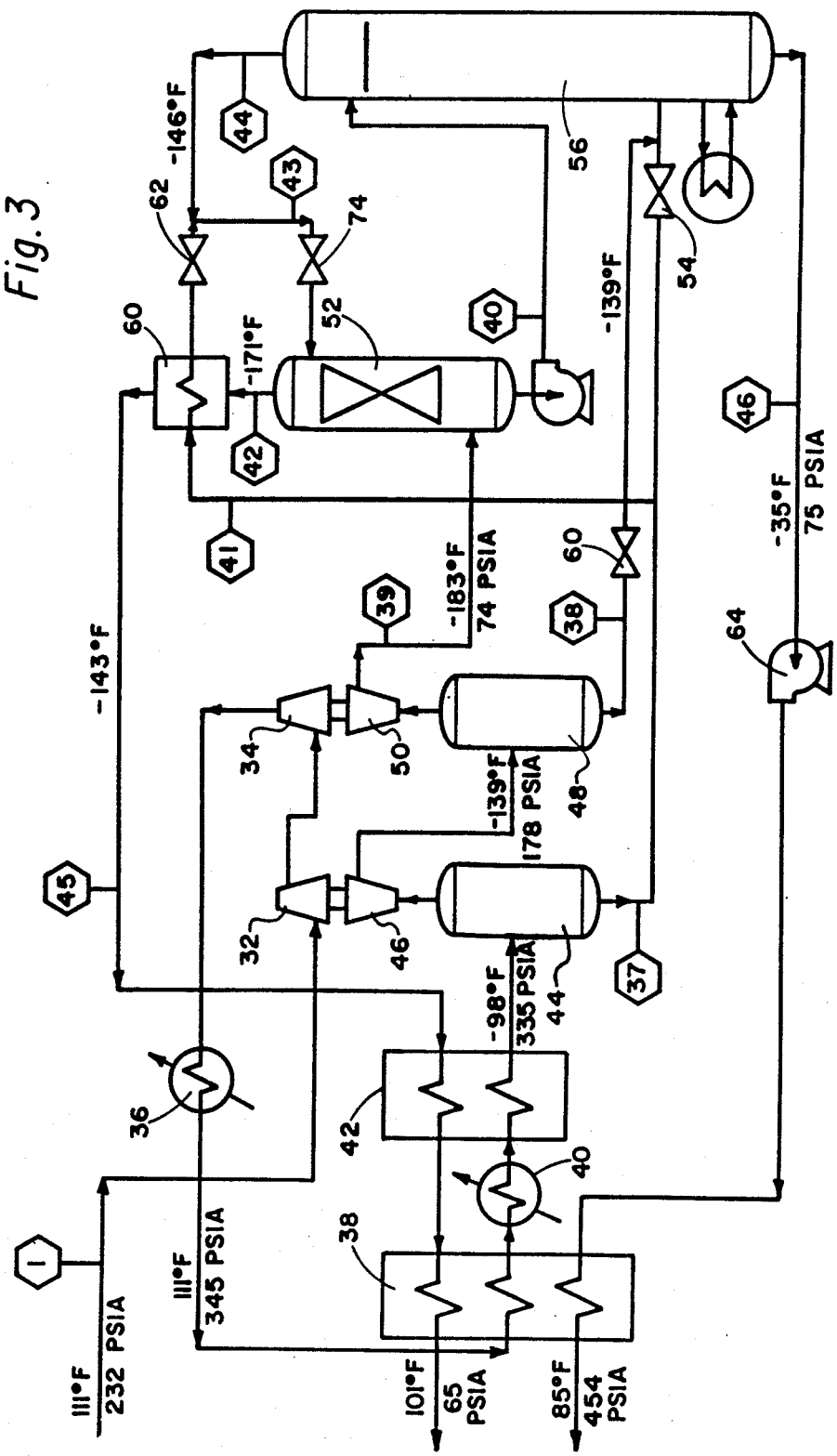

Table 2 which shows the moles per hour calculations of a simulation of the system of FIG. 2 provides a comparison of the contents of the various streams of this FIG. 3 illustrates another alternate embodiment of the process. In this embodiment a portion of the effluent obtained from the first high pressure separator 44 is passed through a heat exchanger 60 and valve 62 before it is co-mingled with the off gas from heavy ends fractionation column 56. The combined effluent and off gas (stream 43) are then conducted through a valve 74 and thence into the upper end of the light ends fractionating column 52. Valves 54 and 62 are used to apportion the quantity of the effluent discharge from the first high pressure separator 44 which is fed into the lower end of the heavy ends fractionation column 56 and into the co-mingled stream which is fed through valve 74 into the light ends fractionating column 52.

Table 3 provides the molar rates of the various streams in the process of the embodiment of FIG. 3 showing the percentage recoveries of ethane and ethylene are substantially identical to those obtained in the embodiment of FIG. 1.

TABLE 3

| INLET GAS | 1 | 37 | 38 | 39 | 40 | STREAM NUMBER 41 MOL/HR | 42 | 43 | 44 | 45 | 46 | PERCENT RECOVERY |
|---|---|---|---|---|---|---|---|---|---|---|---|---|
| Hydrogen | 2022.45 | 3.79 | 0.09 | 2018.57 | 0.65 | 3.79 | 2022.45 | 4.53 | 0.74 | 2022.45 | 0.00 | |
| Nitrogen | 31.57 | 0.25 | 0.01 | 31.32 | 0.10 | 0.25 | 31.57 | 0.36 | 0.11 | 31.57 | 0.00 | |
| Carbon Monoxide | 18.04 | 0.20 | 0.01 | 17.84 | 0.10 | 0.20 | 18.04 | 0.31 | 0.11 | 18.04 | 0.00 | |
| Carbon Dioxide | 6.20 | 1.09 | 0.09 | 5.02 | 2.18 | 1.09 | 4.00 | 1.16 | 0.07 | 4.00 | 2.20 | |
| Methane | 293.47 | 14.10 | 0.76 | 278.61 | 13.11 | 14.10 | 292.62 | 27.12 | 13.02 | 292.62 | 0.85 | |
| Ethylene | 66.25 | 23.78 | 2.01 | 40.47 | 42.85 | 23.78 | 21.81 | 24.19 | 0.42 | 21.81 | 44.44 | 67.08 |
| Ethane | 167.46 | 87.83 | 8.03 | 71.60 | 129.64 | 87.83 | 30.31 | 88.36 | 0.52 | 30.31 | 137.15 | 81.90 |
| Propylene | 23.96 | 21.25 | 1.49 | 1.23 | 22.04 | 21.25 | 0.44 | 21.26 | 0.01 | 0.44 | 23.52 | 98.16 |
| Propane | 79.78 | 72.65 | 4.45 | 2.69 | 74.29 | 72.65 | 1.06 | 72.67 | 0.02 | 1.06 | 78.72 | 98.67 |
| 1-Butene | 5.92 | 5.83 | 0.08 | 0.01 | 5.83 | 5.83 | 0.01 | 5.83 | 0.00 | 0.01 | 5.91 | 99.83 |
| Iso butane | 54.13 | 53.03 | 1.00 | 0.09 | 53.04 | 53.03 | 0.09 | 53.03 | 0.00 | 0.09 | 54.04 | 99.83 |
| Butane | 29.88 | 29.57 | 0.31 | 0.01 | 29.56 | 29.57 | 0.02 | 29.57 | 0.01 | 0.02 | 29.86 | 99.93 |
| Iso pentane | 14.10 | 14.06 | 0.03 | 0.00 | 14.06 | 14.06 | 0.00 | 14.06 | 0.00 | 0.00 | 14.10 | 100.00 |
| Pentane | 5.92 | 5.91 | 0.01 | 0.00 | 5.91 | 5.91 | 0.00 | 5.91 | 0.00 | 0.00 | 5.92 | 100.00 |
| TOTAL mol/hr | 2819.13 | 333.34 | 18.37 | 2467.46 | 393.36 | 333.34 | 2422.42 | 348.36 | 15.03 | 2422.42 | 396.71 | |
| Temperature °F. | 111 | −98 | −139 | −183 | −175 | −98 | −171 | −160 | −146 | −143 | −35 | |
| Pressure, psia | 232 | 335 | 178 | 74 | 75 | 335 | 74 | 74 | 75 | 74 | 75 | |

Figure 4:
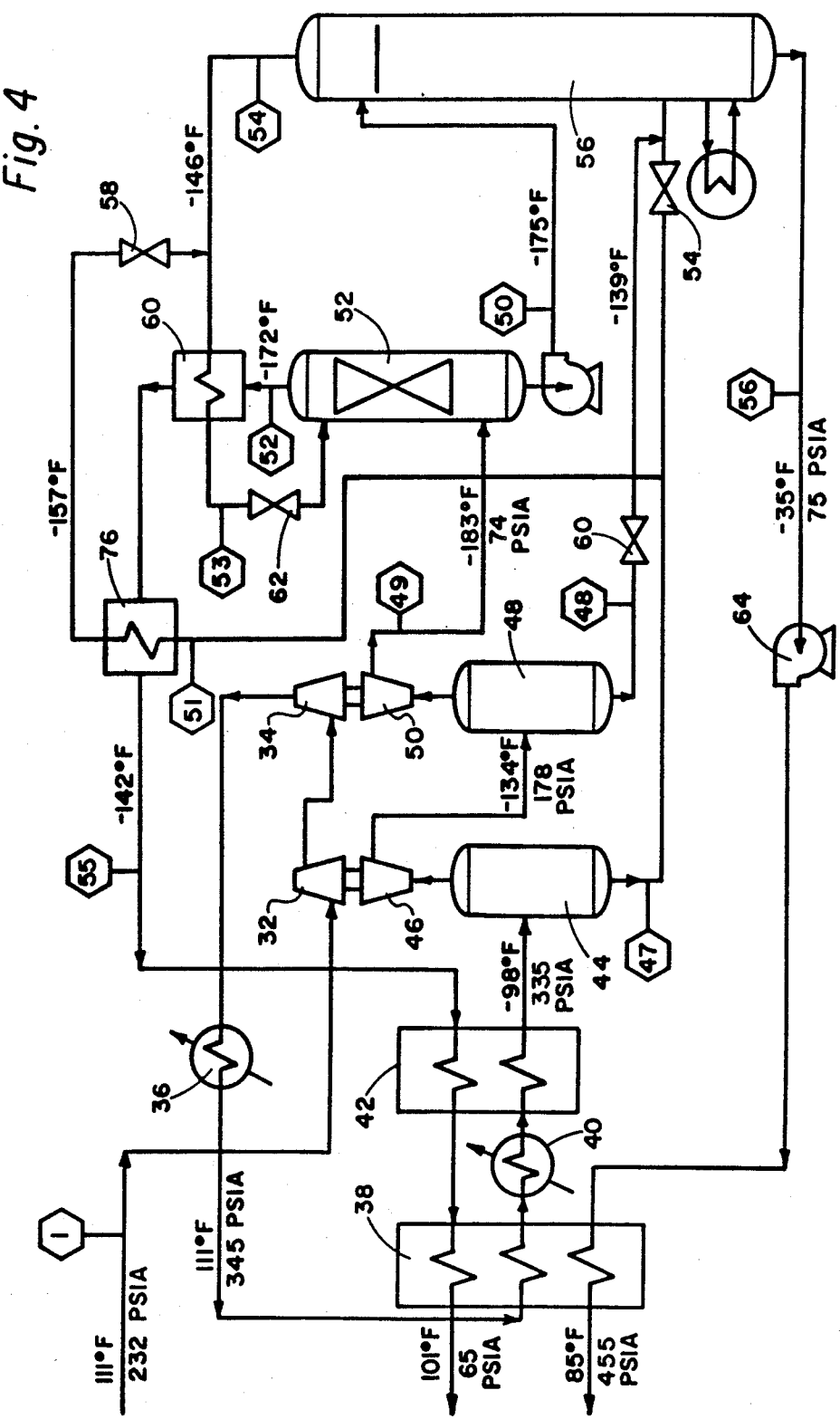

FIG. 4 shows a still different alternate embodiment of the process. An additional heat exchanger 76 is employed through which a portion of the effluent discharge from the high pressure separator 44 is passed before the effluent is co-mingled with the off gas from the heavy ends fractionation column 56. Table 4 shows the calculated moles per hour of the various streams in the embodiment of FIG. 4 and the pressure and temperature of the streams. The percent recovery of ethylene is slightly higher using the process of FIG. 4 compared with that of FIG. 1 and the total hydrocarbon recovery is slightly improved.

The improved process of this invention as exemplified in the embodiments of FIGS. 1 through 4 achieves a given ethane/ethylene recovery while requiring relatively lower inlet gas pressure and refrigeration compression horse power than with the known prior art process. Further, in the processes exemplified in FIGS. 1 through 4 the ethane/ethylene recovery is achieved in a manner wherein the process is operated at a higher

TABLE 4

| INLET GAS | STREAM NUMBER MOL/HR | | | | | | | | | | | PERCENT RECOVERY |
|---|---|---|---|---|---|---|---|---|---|---|---|---|
| | 1 | 47 | 48 | 49 | 50 | 51 | 52 | 53 | 54 | 55 | 56 | |
| Hydrogen | 2022.45 | 3.79 | 0.09 | 2018.57 | 0.65 | 3.79 | 2022.45 | 4.53 | 0.74 | 2022.45 | 0.00 | |
| Nitrogen | 31.57 | 0.25 | 0.01 | 31.32 | 0.10 | 0.25 | 31.57 | 0.36 | 0.11 | 31.57 | 0.00 | |
| Carbon Monoxide | 18.04 | 0.20 | 0.01 | 17.84 | 0.10 | 0.20 | 18.04 | 0.31 | 0.11 | 18.04 | 0.00 | |
| Carbon Dioxide | 6.20 | 1.09 | 0.09 | 5.02 | 2.20 | 1.09 | 3.99 | 1.16 | 0.08 | 3.99 | 2.21 | |
| Methane | 293.47 | 14.10 | 0.76 | 278.61 | 13.17 | 14.10 | 292.71 | 27.28 | 13.17 | 292.71 | 0.76 | |
| Ethylene | 66.25 | 23.78 | 2.01 | 40.47 | 43.20 | 23.78 | 21.46 | 24.20 | 0.42 | 21.46 | 44.79 | 67.61 |
| Ethane | 167.46 | 87.83 | 8.03 | 71.60 | 130.60 | 87.83 | 29.37 | 88.37 | 0.54 | 29.37 | 138.09 | 82.46 |
| Propylene | 23.96 | 21.25 | 1.49 | 1.23 | 22.06 | 21.25 | 0.42 | 21.26 | 0.01 | 0.42 | 23.54 | 98.25 |
| Propane | 79.78 | 72.65 | 4.45 | 2.69 | 74.34 | 72.65 | 1.01 | 72.67 | 0.02 | 1.01 | 78.77 | 98.73 |
| 1-Butene | 5.92 | 5.83 | 0.08 | 0.01 | 5.83 | 5.83 | 0.01 | 5.83 | 0.00 | 0.01 | 5.91 | 99.83 |
| Iso butane | 54.13 | 53.03 | 1.01 | 0.09 | 53.04 | 53.03 | 0.08 | 53.03 | 0.01 | 0.08 | 54.05 | 99.85 |
| Butane | 29.88 | 29.57 | 0.31 | 0.01 | 29.56 | 29.57 | 0.01 | 29.57 | 0.00 | 0.01 | 29.87 | 99.97 |
| Iso pentane | 14.10 | 14.06 | 0.04 | 0.00 | 14.06 | 14.06 | 0.00 | 14.06 | 0.00 | 0.00 | 14.10 | 100.00 |
| Pentane | 5.92 | 5.91 | 0.01 | 0.00 | 5.91 | 5.91 | 0.00 | 5.91 | 0.00 | 0.00 | 5.92 | 100.00 |
| TOTAL mol/hr | 2819.13 | 333.34 | 18.39 | 2467.46 | 394.82 | 333.34 | 2421.12 | 348.54 | 15.21 | 2421.12 | 398.01 | |
| Temperature °F. | 111 | −98 | −139 | −183 | −175 | −98 | −172 | −163 | −146 | −142 | −35 | |
| Pressure, psia | 232 | 335 | 178 | 74 | 75 | 335 | 74 | 74 | 75 | 74 | 75 | |

The process has been illustrated using various standard components employed for the sequence of treating steps with it being understood that the process may be practiced utilizing different physical apparatus. For instance, the turbo expanders 46 and 50 can in many instances be replaced by Joule-Thomson isenthalpic control valves. The difference is that where the Joule-Thomson valves are substituted for the turbo expanders, normally greater inlet and refrigeration compression duties are required.

Various arrangements have been shown in the alternate embodiments for cooling the second residue effluent and, in some instances, the combined residue effluent and heavy ends fractionation column off gas; however, it has been determined that the resultant $C_2$ recovery is essentially identical provided an equal amount of heat is removed in any of the various embodiments of the process which have been described.

The illustrated processes in each instance use two turbo expanders. The desirability of the use of multiple turbo expanders is predicated primarily upon the amount of hydrogen content of the inlet gas in stream 1. It is understood that, according to the inlet gas content, only single turbo expanders may be employed in practicing the process; or, in some instances as previously indicated, turbo expanders may be eliminated completely and substituted by one or more Joule-Thomson isenthalpic expansion valves.

An important element of the process is the employment of the light ends fractionating column 52 which functions as a combination heat and mass transfer device. The use of the reflux in the top stage means that the liquid methane of the reflux is vaporized; and in turn the liquid is progressively enriched in ethylene and ethane condensed from the upflowing bottom feed vapors to thereby recover a higher percent of the $C_2$ components.

For a given ethane/ethylene recovery, the process allows reducing the pressures that were required in the first cold separator; thus reducing the inlet compression capital and operating costs compared to the prior art.

temperature level than in the previously known processes. As an added benefit, the processes of FIGS. 1 through 4 are slightly less susceptible to carbon dioxide freezing than previously known processes.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An improved process for separating a hydrocarbon bearing feed gas containing ethane and $C_2$ (ethylene and/or ethane) components into a fraction containing predominantly methane and lighter components and a fraction containing a predominant portion of the $C_2$ and heavier components, comprising the steps of:

(a) cooling and partially condensing the feed gas and delivering it to a separator to provide thereby a first residue vapor and a $C_2$-containing liquid, which liquid also contains lighter hydrocarbons including appreciable methane;

(b) directing at least part of the $C_2$-containing liquid into a heavy ends fractionation column wherein said liquid is separated into a second hydrocarbon bearing residue vapor containing predominantly methane and a $C_2$-containing product;

(c) passing the second residue through a heat exchanger to condense at least a major portion of the methane content thereof;

(d) contacting at least part of said first residue vapors with at least part of the partially condensed second residue in a light ends fractionation column to thereby obtain third residue vapors and liquids;

(e) supplying the liquids thereby recovered from the light ends fractionating column to the heavy end fractionation column as a liquid feed thereto; and (f) directing at least part of the $C_2$-containing liquid from step (a) into intimate contact with the second residue prior to step (d), which liquid provides additional liquefied methane which acts with said partially condensed second residue as a direct contact refrigerant to thereby condense $C_2$ and heavier components while the methane itself is evaporated in the light ends fractionation column.

2. The improved process according to claim 1 wherein the light ends fractionation column of step (c) includes fractionation means for vapor-liquid counter-current contact wherein said partly condensed second residue in conjunction with at least a portion of the $C_2$ containing liquid from step (a) is introduced into said light ends fractionation column above said fractionation means, whereby the liquid portion of it passes downwardly through said fractionation means and said first residue vapors is supplied to said light ends fractionation column below said fractionation means, whereby the first residue vapor rises through said fractionation means in counter-current contact with the liquid portion of the partly condensed second residue and said $C_2$ containing liquid admixed therewith in step (e).

3. The improved process according to claim 2 wherein the fractionation means in said light ends fractionation column provide the equivalent of at least one theoretical distillation stage arranged to contact at least part of said first residue vapors with the liquid portion of the partly condensed second residue and said $C_2$ containing liquid admixed therewith in step (e).

4. The process of claim 1 including the step of: cooling the $C_2$-containing liquid from step (a).

5. The proces of claim 1 including the step of: cooling the combined second residue and $C_2$-containing liquid from step (a) before the same is delivered into the light ends fractionation column.

6. The process of claim 1 including the step of: directing the third residue recovered from the light ends fractionation column into heat exchange relation with said second residue from the heavy end fractionation column.

7. The process of claim 1 including the step of: passing the first residue from step (a) through an expansion means to decrease the pressure and reduce the temperature of the first residue before the same is delivered to the light ends fractionation column.

8. The process of claim 1 including the step of reducing the temperature of the second residue before the same is directed into contact with at least part of the $C_2$-containing liquid from step (a) in step (e).

9. The process of claim 8 wherein the step of reducing the temperature of the second residue includes the steps of:

(a) passing the second residue through a heat exchanger;

(b) compressing the second residue after step (a);

(c) expanding the compressed residue of step (b) to reduce the temperature thereof;

(d) passing the reduced temperature residue of step (c) through the heat exchanger of step (a); and (e) directing the second residue from step (d) into contact with at least part of the $C_2$-containing liquid in step (e).

10. An apparatus for separating a hydrocarbon feed gas containing at least methane and $C_2$ components into a fraction containing a predominant portion of methane and lighter components and a fraction containing a predominant portion of the $C_2$ and heavier components, comprising:

(a) separator means for receiving hydrocarbon feed gas and for providing at a first outlet a first residue vapor and at a second outlet $C_2$-containing liquid, which liquid also contains lighter hydrocarbons;

(b) a heavy ends fractionation column means connected to receive at least a portion of said $C_2$-containing liquids, the heavy ends fractionation column means being adapted to separate the $C_2$-containing liquids into a second residue containing lighter hydrocarbons and a $C_2$-containing liquid product;

(c) light ends fractionation column means connected to receive at least part of said first residue vapors and at least part of the liquid portion of the partially condensed second residue and to co-mingle said vapor and liquid in at least one contacting stage, and including separation means for separating the vapor and liquid after contact in said stage, and being further connected to supply the liquids separated therein to said heavy end fractionation column means as a liquid feed thereto; and (d) means of co-mingling at least a portion of said $C_2$-containing liquid from said separator means with said second residue before said second residue is introduced into said light ends fractionation column means.

11. The apparatus according to claim 10 wherein said light ends fractionation column means includes fractionation means for counter-current vapor-liquid contact and wherein said light ends fractionation column means is connected to receive the portion of said first residue vapors to be treated therein below said fractionation means and to receive the portion of said liquids from the partially condensed second residue to be treated therein above said fractionation means, said fractionation means thereby being adapted so that the first residue vapors rise therethrough in counter-current contact with partially condensed second residue.

12. The apparatus according to claim 11 wherein said fractionation means in said light ends fractionation column means includes vapor-liquid contacting means which are the equivalent of at least one theorretical distillation stage.

13. An apparatus according to claim 10 including: heat exchange means connected to receive said second residue and to partially condense it.

14. An apparatus according to claim 13 wherein said heat exchange means connected to receive said second residue and to partially condense it includes the arrangement wherein said light ends fractionation column means is connected to direct third residue vapors separated therein through said heat exchange means.

15. An apparatus according to claim 10 including: expansion means connected to receive first residue from said separator means having means to reduce the pressure of and reduce the temperature of the first residue before the same is directed into said light ends fractionation column means.

16. An apparatus according to claim 15 wherein said expansion means is in the form of a turbo expander.

* * * * *

UNITED STATES PATENT AND TRADEMARK OFFICE
CERTIFICATE OF CORRECTION

PATENT NO. : 4895584
DATED : Jan. 23, 1990
INVENTOR(S) : Loren L. Buck and Ronald D. Key It is certified that error appears in the above-indentified patent and that said Letters Patent is hereby corrected as shown below:

Col. 9, line 21, change "(c)" to --(d)--;
Col. 9, line 40, change "(e)" to --(f)--;
Col. 9, line 60, change "(e)" to --(f)--.

Signed and Sealed this

Twenty-fifth Day of July, 1995

Attest:

BRUCE LEHMAN

Attesting Officer

Commissioner of Patents and Trademarks